Figure 1:
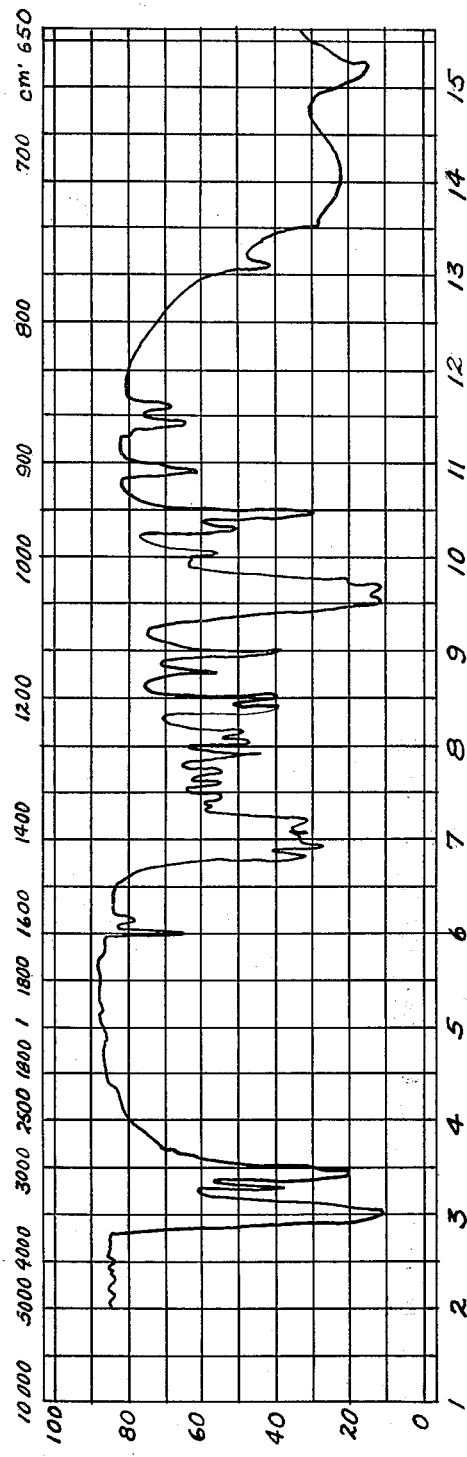
Figure 2:
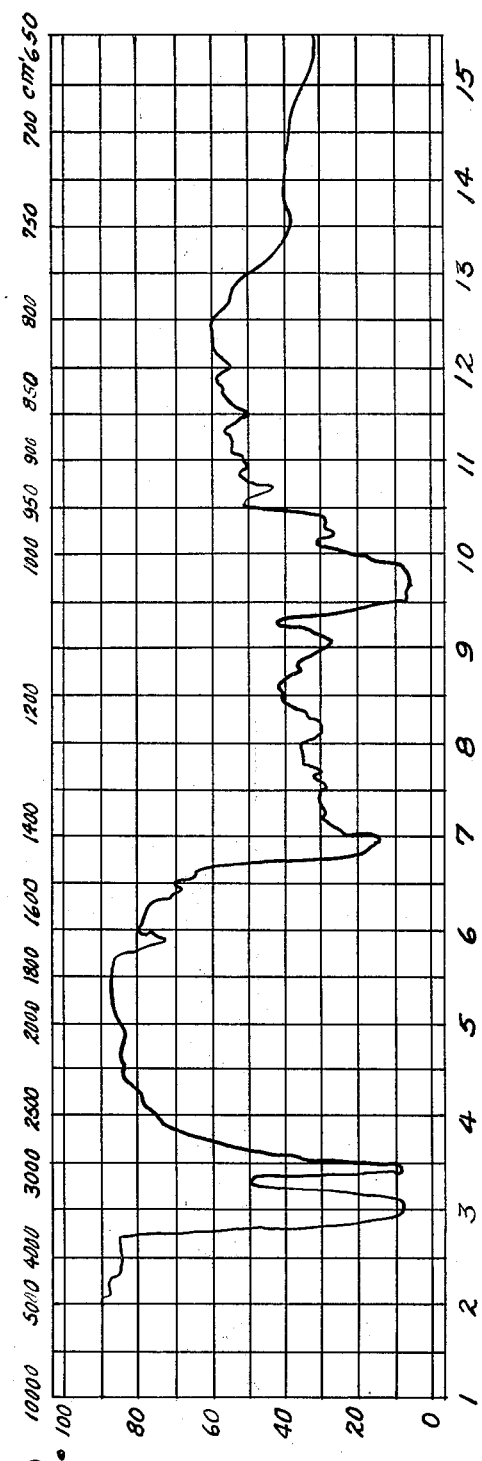

United States Patent [19]

Schwarze et al.

[11] 3,968,074
[45] July 6, 1976

[54] REACTION PRODUCT OF 4,4-BIS-(HYDROXYMETHYL)-CYCLOHEXENE COMPOUNDS WITH SULFUR

[75] Inventors: Werner Schwarze, Frankfurt; Siegfried Wolff, Bornheim-Merten, both of Germany

[73] Assignee: Deutsche Gold- und Silber-Scheideanstalt vormals Roessler, Germany

[22] Filed: Feb. 7, 1975

[21] Appl. No.: 548,218

[30] Foreign Application Priority Data
Apr. 22, 1974  Germany............................ 2419235

[52] U.S. Cl............................. 260/42.24; 106/288 B; 106/293; 106/300; 106/306; 260/42.29; 260/42.32; 260/42.33; 260/42.36; 260/42.37; 260/42.43; 260/42.47; 260/125; 260/765; 526/194; 526/204; 526/211; 526/217; 526/222; 526/338; 526/339; 526/334; 526/916; 526/30
[51] Int. Cl.²..................... C07G 17/00; C08K 3/04; C08K 3/06; C08K 3/36
[58] Field of Search................ 260/125, 608, 609 F, 260/42.24, 42.29, 42.32, 42.33, 42.36, 42.37, 42.43, 42.47, 80.7, 82.3, 83.5, 83.7, 85.3 R, 94.2 R, 765; 106/288 B, 293, 300, 306

[56] References Cited
UNITED STATES PATENTS

| | | | |
|---|---|---|---|
| 2,989,513 | 6/1961 | Hendry et al. ..................... | 260/125 |
| 3,064,056 | 11/1962 | Ebersberger et al. ............... | 260/608 |
| 3,632,566 | 1/1972 | Coleman ............................ | 260/125 |
| 3,801,537 | 4/1974 | Westlinning et al. ............. | 260/42.33 |
| 3,842,111 | 10/1974 | Meyer-Simon et al. ....... | 260/448.2 E |

*Primary Examiner*—Donald E. Czaja
*Assistant Examiner*—H. H. Fletcher
*Attorney, Agent, or Firm*—Cushman, Darby & Cushman

[57] ABSTRACT

There are prepared reaction products of a. 4,4-bis-(hydroxymethyl)-cyclohexene compounds of the formula

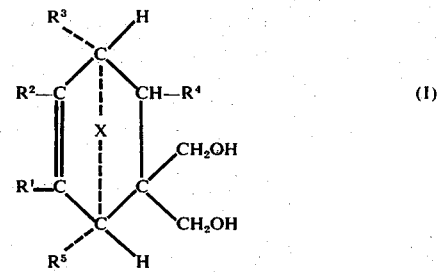

(I)

where $R^1$, $R^2$ and $R^4$ are the same or different and are hydrogen, methyl or phenyl and there is also present either (1) X as the bridging member methylene or ethylene or (2) X is absent and there are present both $R^3$ and $R^5$ wherein $R^3$ and $R^5$ are the same or different and are hydrogen, methyl or phenyl with (b) sulfur. The compounds are useful in cross-linking vulcanizable elastomers.

35 Claims, 4 Drawing Figures

REACTION PRODUCT OF 4,4-BIS-(HYDROXYMETHYL)-CYCLOHEXENE COMPOUNDS WITH SULFUR

The invention is directed to reaction products.

There are prepared reaction products of (a) 4,4-bis-(hydroxymethyl)-cyclohexene compounds of the formula

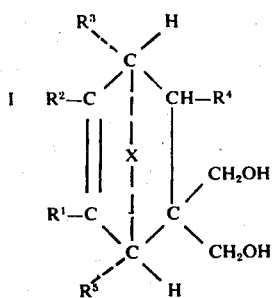

in which $R^1$, $R^2$ and $R^4$ are the same or different and represent hydrogen, methyl or phenyl and there is also present either (1) X as the bridging member representing methylene or ethylene or (2) X is absent and there are present both $R^3$ and $R^5$ whereby $R^3$ and $R^5$ are the same or different and represent hydrogen, methyl or phenyl with (b) sulfur. The exact structure of the compounds of the invention is not known.

The starting compounds employed in the invention for reaction with sulfur can also be expressed by the following two formulae:

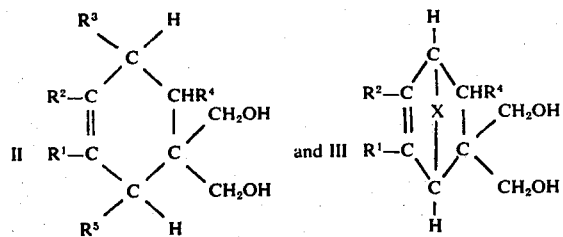

The starting compounds of formula I which also can be designated geminal dimethylol compounds or as alcohols are known for the greatest part. They can be produced from the corresponding Δ3 unsaturated aldehydes and formaldehyde according to the Cannizzaro reaction employing alkalis. The unsaturated aldehydes are obtained according to the Diels-Alder reaction from a diene and an unsaturated aldehyde. Examples of dienes (always conjugated) are butadiene-1,3, pentadiene-1,3, 2-methylbutadiene, 2,3-dimethyl butadiene, 2-methyl pentadiene-1,3,trimethyl butadiene (1,2,3-trimethyl butadiene-1,3), tetramethyl butadiene (3,4-dimethyl hexadiene-2,4), 1-phenyl butadiene, hexadiene-2,4, cyclopentadiene, cyclohexadiene, 1-methyl cyclohexadiene, etc. As aldehydes there can be used for example acrolein, crotonaldehyde and cinnamaldehyde.

Examples of compounds within formula I are 4,4-bis-(hydroxymethyl)-cyclohexene, 3,6-methano-4,4-bis-(hydroxymethyl)-cyclohexene (4,4-bis-(hydroxymethyl)-bicyclo [2,1,2]-heptene-1), 3,6-ethano-4,4-bis-(hydroxymethyl) cyclohexene, 1-methyl-3,6-methano-4,4-bis-(hydroxymethyl)-cyclohexene, 1-methyl-4,4-bis-(hydroxymethyl) cyclohexene, 4,4-bis-(hydroxymethyl)-5-methyl cyclohexene, 2-methyl-4,4-bis-(hydroxymethyl)-cyclohexene, 3-methyl-4,4-bis-(hydroxymethyl)-cyclohexene, 6-methyl-4,4-bis-(hydroxymethyl-cyclohexene, 4,4-bis-(hydroxymethyl)-5-phenyl cyclohexene, 1,2,5-trimethyl-4,4-bis-(hydroxymethyl)-cyclohexene, 1,2,3,4-tetramethyl-4,4-bis-(hydroxymethyl)-cyclohexene, 1,2,3,4,5-pentamethyl-4,4-bis-(hydroxymethyl)-cyclohexene, 3,5-diphenyl-4,4-bis-(hydroxymethyl)-cyclohexene, 3-phenyl-4,4-bis-(hydroxymethyl)-cyclohexene, 3-phenyl-5-methyl-4,4-bis-(hydroxymethyl)-cyclohexene, 1-methyl-5-phenyl-4,4-bis-(hydroxymethyl)-cyclohexene.

The reaction of the above named dimethylol compounds within formula I with sulfur can take place in the presence or absence of inert organic solvents. Preferably, however, the reaction is carried out in the absence of a solvent.

The reaction temperature is adjusted according to whether the operation is carried out in a solvent or without a solvent. In the direct reaction without a solvent it is necessary to use temperatures above 100°C. Preferably the reaction temperature is between 120° and 160°C. The upper temperature can be about 200°C. or in a given case somewhat higher.

When a solvent is employed the same temperatures can be employed or even somewhat lower temperatures, e.g. 80°C. A convenient temperature is the reflux temperature for the solvent. Typical inert solvents include aromatic hydrocarbons such as benzene, toluene and xylene. Other suitable solvents include chlorobenzene, naphthalene, alkyl($C_1$–$C_5$) substituted naphthalenes, cumene, anisole and other phenolic ethers.

In the reaction the sulfur attacks the double bond of the cyclohexene ring. Thereby there are formed mono and polysulfides of a highly complex structure. According to the amount of sulfur added there are formed compounds with different sulfur contents. Accordingly, the ratio of diol to sulfur can be varied within quite wide ranges, for example, molar ratios between about 1:0.1 and 1:20. Preferably the molar ratio of diol to sulfur is in the range from 1:1 and 1:8. Depending upon the amount of sulfur taken the reaction products formed up are highly viscous oils, some of which solidify when cold up to oligomers with properties similar to rosin.

The course of the reaction of the dimethylol compounds with the sulfur according to the invention can be followed by IR-measurements. Thus, for example, it is possible in the case of sulfurization of 4,4-bis-(hydroxymethyl)-cyclohexene to evaluate the ratio of the maximum absorbance values of the olefinic and cycloaliphatic CH-stretching vibrational bands at 3015 and 2920 $cm^{-1}$ and also the ratio of the maximum absorbance values of the —C=C— band at 1650 $cm^{-1}$ and of the —$CH_2$— deformation vibrational band at 1440 $cm^{-1}$. In the NMR spectrum (NMR is magnetic nuclear resonance) in analogous manner the ratio of the area of the =CH— signal to the area of the —CH— plus —$CH_2$— signals is a corresponding measure.

It can be assumed that in the reaction there are formed primarily polysulfides of the alkyl alkenyl polysulfide type which then can be split up in secondary reactions into a number of sulfurization products. Indications in support of this explanation of the reaction may be found, for example, in the book, "Chemistry and Physics of Rubber-like Substances" by L. Bateman, published in 1973 by Maclaren and Sons Ltd., pages 449 et seq. Attention is also directed to "Mechanism of Sulfur Reactions" by William A. Pryor, McGraw-Hill Book Company, Inc. (1962) Chapter 5, "The reactions of Sulfur with Olefins to Produce Organic Sulfides and Polysulfides." Further references include "The Chemistry of Organic Sulphur Compounds" by Norman Kharasch and Cal Y. Meyers, Volume 1, chapter 20, "Reactions of Sulphur With Olefins" by L. Bateman and C. G. Moore pages 210 to 228; R. T. Armstrong, J. R. Little and K. W. Doak, Industrial and Engineering Chemistry, Volume 36, pages 628–633 (1944); M. L. Selker and A. R. Kemp, Industrial and Engineering Chemistry Volume 39, pages 895 et seq. (1947); E. H. Farmer and F. W. Shipley, J. Chem. Soc. (London) pages 1519–1532 (1947); A. S. Brown, M. G. Voronkov and K. P. Kashkova, Zh. Obschcher Khim (Russian), Volume 20, pages 726 et seq. (1950).

Unless otherwise indicated all parts and percentages are by weight.

Examples of the reaction according to the invention include

1. Sulfurization of 4,4-bis-(hydroxymethyl)-cyclohexene in the molar ratio of alcohol to sulfur of 1:2.

There is melted in a 10 liter flask equipped with a stirrer and placed in an oil bath 6 kg of 4,4-bis-(hydroxymethyl)-cyclohexene and the material heated to 130°to 135°C. At this temperature there is introduced into the melt within about 3 hours 2.7 kg of sulfur powder. The reaction is initially slightly exothermic. The course of the reaction is followed by IR analysis. After a further 60 minutes the temperature is increased to 145° to 150°C. After a total of 8 hours of reaction the sulfurization was complete.

The at first viscous, dark brown oil formed is poured on a plate and allowed to solidify in the air. The solidified mass can be broken, comminuted or ground for further use. There were obtained 8.61 kg of reaction product with a sulfur content of 31 weight percent. The brown powder upon heating to about 50°C becomes plastic and melts at about 95°C.

The same cyclohexene starting product can be reacted in an analogous way with sulfur for example in the molar ratios of 1:1, 1:1.5, 1:3, 1:6; 1:8; 1:10; 1:20, etc. Thereby the reaction time can be varied, for example it can be increased.

2. Reaction of 4,4-bis-(hydroxymethyl)-cyclohexene with sulfur in the molar ratio of 1:8.

There were heated to 135°C. as described in example 1 above 142 grams of 4,4-bis-(hydroxymethyl)-cyclohexene and then there were introduced with stirring a total of 256 grams of sulfur in powder form within 8 hours. Then the melt was heated for 16 more hours at 145° to 150°C.

The at first highly viscous reaction product was poured in a dish and allowed to solidify to a stone hard mass. There was obtained the reaction product in an amount of 381.5 grams and it had a sulfur content of 65.2%. The dark brown powder melted at about 110°C.

3. Reaction of 4,4-bis-(hydroxymethyl)-cyclohexene with sulfur in the mole ratio of 1:4 in xylene.

There were provided in a 2-liter round-bottomed flask equipped with a reflux condenser 1 liter of xylene and 142 grams of 4,4-bis-(hydroxymethyl)-cyclohexene, 128 grams of sulfur in powder form and 2 ml of tributylamine. The mixture was boiled under reflux for 12 hours and subsequently evaporated in a vacuum, terminal conditions being 100°C. and a pressure of 12 mm Hg. There were obtained 269.5 grams of a dark brown oil, which solidified in the cold, and according to the analysis contained 47.1 weight percent sulfur.

4. Reaction of 3,6-Methano-4,4-bis-(hydroxymethyl)-cyclohexene [4,4-bis-(hydroxymethyl)-bicyclo [2,1,2]-heptene-1] having a melting point of 111° to 114°C. with sulfur in the mole ratio of 1:4.

154 grams of the geminal diol were melted in a 500 ml round-bottomed flask and heated to 130°C. With stirring there were added 128 grams of sulfur within 6 hours and the mixture subsequently heated a further 20 hours to 145° to 150°C., the reaction product was subsequently poured into a mortar and pulverized. There was obtained a brown powder in an amount of 271 grams with a melting point of about 95° to 100°C. and a sulfur content of 45.5 weight %. In an analogous reaction there was also recovered the reaction product of 1 mole of cyclohexene with 8 moles of sulfur. Differences between the starting material and reaction product were observed in the IR-spectrum.

In place of the 3,6-methano compound there can also be employed 3,6-ethano-4,4-bis-(hydroxymethyl)-cyclohexene and reacted with sulfur in an analogous way in the desired mole ratio.

5. Reaction of 1-methyl-4,4-bis-(hydroxymethyl)-cyclohexene with sulfur in the mole ratio of 1:1.

There were melted 78 grams of 1-methyl-4,4-bis-(hydroxymethyl)-cyclohexene in a round bottomed flask and there were introduced into the melt with stirring at about 130°C. within 3 hours, 16 grams of sulfur. After heating for five hours at 140° to 145°C. the double bond in the cyclohexene ring had disappeared as shown by IR measurement. There was obtained a viscous resin having an amber-like appearance in an amount of 82 grams. The analysis showed a sulfur content of 17 weight percent.

6. Reaction of 4,4-bis-(hydroxymethyl)-cyclohexene with sulfur in the mole ratio of 1:6.

There were mixed 156 grams of 4,4-bis-(hydroxymethyl)-5-methyl-cyclohexene with 192 grams of sulfur and 1 gram of tributylamine and the mixture was then heated with stirring for 18 hours at 140° to 150°C. There was obtained a dark brown melt which solidified below 100°C. in an amount of 341 grams. The sulfur analysis was 54.1 weight percent.

In the same manner there can also be reacted with sulfur 2-methyl-4,4-bis-(hydroxymethyl)-cyclohexene, 3-methyl-4,4-bis-(hydroxymethyl)-cyclohexene and 4,4-bis-hydroxymethyl)-6-methyl-cyclohexene.

7. Reaction of 4,4-bis-(hydroxymethyl)-5-phenyl-cyclohexene with sulfur in the mole ratio of 1:3.

218 grams of 4,4-bis-(hydroxymethyl)-5-phenyl-cyclohexene and 96 grams of sulfur were stirred and heated for 16 hours at 140°–145°C.

The dark brown melt solidified at about 75°C. The amount of product was 306.5 grams and contained 30.1 weight percent of sulfur.

8. Reaction of 1,2,5-trimethyl-4,4-bis-(hydroxymethyl)-cyclohexene with sulfur in the mole ratio of 1:5.

184 grams of 1,2,5-trimethyl-4,4-bis-(hydroxymethyl)-cyclohexene were heated with stirring to about 135°C. With further stirring there were added within 4 hours at the same temperature 120 grams of sulfur and stirring continued for another 12 hours at this temperature.

The working up of the reaction product produced 298.5 grams of a brown product which solidified at about 70°C. The analysis showed a sulfur content of 39.5 weight percent.

The reaction products of the invention have a different sulfur content depending on the amount of sulfur added in relation to the amount of alcohol. However, the individual products are produced reproducably, especially in checking the course of the reaction by IR analysis, which also can be gathered from the combustion analysis.

The new reaction products can, as has been unexpectedly proven, be used with outstanding success as reinforcing additives in the rubber processing industry with both natural and synthetic rubbers containing light fillers such as, for example, silica.

With these types of rubber mixtures there is the industrial problem that under the influence of light reinforcing fillers the viscosity of the raw mixtures can be very high and therewith there is increased difficulty in working the mixtures during the processes of production. This increase in viscosity is related to the amount and activity of the filler. The more active the fillers the higher is the viscosity of the mixtures and therewith the more difficult the workability.

There is already known an entire series of additives in the industry which have as the object the reduction of the viscosity of the raw mixtures. For this purpose there have been added for example glycol, hexanetriol, polywaxes and other compounds. A serious disadvantage of these compounds is that in order to cause a noticeable reduction in viscosity they must be added in large amounts. However, this has the consequence that the industrial properties of the mixtures produced with the addition of these components of the mixture and the vulcanizates produced become impaired. This is especially noticeable in the reduction of the stress values at 300% elongation (300 Modulus), an important property for the industrial characterization of vulcanizates.

The reaction products of the invention have proved themselves as reinforcing additives and especially possess the properties of strongly reducing the viscosity of the unvulcanized mixtures. With help of the new reinforcing additives there are even workable those mixtures which contain for example a highly active silica with an average primary particle size of 18nm (nanometers) and a surface area of 210m$^2$/g measured according to the known BET-method (Ultrasil VN 3 of Degussa), even in large amounts, for example more than 50 parts by weight per 100 parts by weight of elastomer.

In comparison to the previously employed additives for reduction of the viscosity the new reinforcing additives have no negative influence on the level of properties of the vulcanizate. Unexpectedly the addition of the new reinforcing additives improves tensile strength, modulus, Shore hardness, elasticity and abrasion resistance of the vulcanizates.

It is further surprising that the hydrophilic properties of the vulcanizate which are already present through the addition of the light reinforcing filler are considerably increased by the addition of the new reinforcing additive, which for example makes itself known in wet skid resistance and the favorable behavior on ice of treads as well as of vehicle tires.

There are included in the light or white fillers usable in elastomer mixtures with the reaction products of the invention the following:

Silicas of every activity and fillers containing predominant amounts of silica, in amounts of 1 to 500 parts by weight, preferably 40 to 250 parts by weight, based on 100 parts by weight of the elastomer, silicates of every activity (e.g., aluminum silicate or alkaline earth silicates such as magnesium silicate and calcium silicate) in amounts of 1 to 1000 parts by weight, preferably 10 to 500 parts by weight based on 100 parts by weight of the elastomer, silicatic products such as for example glass fibers and glass fiber products, for example, webs, mats, strands, fabrics, non-woven fabrics and the like as well as glass micro spheres (microballoons).

In the named silicas there are especially considered finely divided, very pure silica with specific surface areas in the range of about 5 to 1000, preferably 20 to 400 m$^2$/g, determined with gaseous nitrogen according to the known BET method and with average primary particle sizes of about 10 to 400 nm, which can be produced for example by precipitation from solutions of silicates, by hydrolytic and/or oxidative high temperature reaction (also called flame hydrolysis), from volatile silicon-halides, e.g., silicon tetrachloride, or by an electric arc process. These silicas in a given case can also be present as mixed oxides or oxide mixtures with oxides of the metals aluminum, magnesium, calcium or zinc.

In the named silicates there are included both natural and synthetic silicates, especially silicates of magnesium, calcium and/or aluminum as fillers which contain these components in predominant amount. Among the natural silicates are included for example Kaolin and natural silicas. The synthetic silicates such as aluminium, magnesium or calcium silicate have specific surface areas of about 20 to 400 m$^2$/g and primary particle sizes of about 10 to 400nm.

Light reinforcing fillers also include finely divided oxides of aluminum and titanium as well as their mixed oxides as well as their mixed products with silicates and/or silicas, which fillers are added in amounts of 1 to 1000, preferably 10 to 500 parts by weight based on 100 parts by weight of the elastomers.

Among the light or white fillers which are known and used in the rubber processing industry are also included chalks, modified calcium carbonates, siliceous chalks, barite, lithopone and the like, which likewise are used in amounts of 1 to 1000 parts by weight preferably 10 to 800 parts by weight based on 100 parts by weight of the elastomers.

The above named light fillers can be used individually or several can be used together in the elastomer mixtures. Additionally carbon black can be added, especially the known rubber carbon blacks, namely in amounts of 0.05 to 50 parts by weight based on 100 parts by weight of the elastomer.

Typical examples of light reinforcing fillers usable in the invention are for example silicas or silicates with the trademarks Aerosil, Ultrasil, Silteg, Durosil, Extrusil and Calsil made and sold by Degussa.

Furthermore there can be added to the rubber mixtures various additives that are used in the rubber industry and further described below.

There are several advantages in not adding the reinforcing additive as such to the rubber mixture but instead first preparing a mixture of at least one filler and at least one of the reaction products of the invention and then, or still later, mixing this mixture with the remaining constituents of the rubber mixture in the usual way and with the help of known mixing apparatus until homogeneous distribution occurs.

The new reaction products (reinforcing additives) of the invention can be added individually or as mixtures of several of them into the elastomer mixtures in amounts of 0.05 to 100 parts by weight, preferably in the range between 0.5 and 25 parts by weight based on 100 parts by weight of the elastomer.

As the elastomers there can be used especially those which can be cross-linked with sulfur or peroxides. Thus there can be used one or more natural or synthetic rubbers in admixture, in a given case oil extended rubber, especially diene elastomers such as natural rubber polybutadiene, polyisoprene, e.g., cis-polyisoprene, butadiene styrene copolymer, butadiene-acrylonitrile copolymer, butadiene vinyl pyridine copolymer, polymerized 2-chlorobutadiene, carboxyl rubber, transpolypenteneamer, butyl rubber, halogenated butyl rubber such as chlorinated butyl rubber and brominated butyl rubber as well as other known diene rubbers as for example terpolymers of ethylene, propylene and for example non-congugated polyenes, e.g., ethylene-propylene-cyclooctadiene, ethylene-propylene-norbornadiene, ethylene-propylene-dicyclopentadiene and ethylene-propylene-cyclododecatriene.

The mixtures of elastomers, rubber, the cross-linking system, the light fillers and the sulfur-containing reaction products of the invention can also include in a given case known vulcanization accelerators as well as in a given case one or more compounds of the group of anti-agers, heat stabilizers, light stabilizers, ozone stabilizers, processing aids, plasticizers, adhesive agents, foaming agents, dyes, pigments, waxes, extenders, as for example, sawdust, organic acids as for example stearic acid, benzoic acid or salicylic acid, additionally lead oxide or zinc oxide, activators as for example triethanolamine, polyethylene glycol or hexanetriol which collectively are known in the rubber industry and rubber art. For the cross-linking or vulcanization there are generally mixed into the mixtures cross-linking agents as especially peroxides, sulfur or in special cases magnesium oxide.

According to the height of the sulfur content of the reaction products of the invention the customary amount of sulfur required for the vulcanization can be reduced. It is suitable and in most cases associated with advantages to carry out the vulcanization with addition of very small amounts of sulfur because the addition of lower amounts of sulfur favorably influences the vulcanization characteristics. Low amounts of sulfur means in this case about 0.2 to 0.5 parts by weight of sulfur per 100 parts by weight of the elastomers. Higher or lower amounts of sulfur are not excluded.

It can be of especial advantage for the vulcanization and the properties of the vulcanizate if there are used as the vulcanization accelerator one or more triazine compounds containing sulfur in their molecule as set forth in German Pat. No. 1,669,954 and Westlinning U.S. Pat. No. 3,801,537. The entire disclosure of the Westlinning U.S. Patent is hereby incorporated by reference and relied upon. Thus there can be used, for example, 2-ethylamino-4-diethylamino-6-mercaptotriazine, 2-ethylamino-4-isopropylamino-6-mercaptotriazine and/or bis-(2-ethylamino-4-diethylamino-triazin-6-yl)-disulfide or any of the other triazines shown in Westlinning, for example those set forth in the table on columns 5–6, lines 3–33 and also column 5, lines 34 to column 8, line 50. Thus the triazines can have the formula

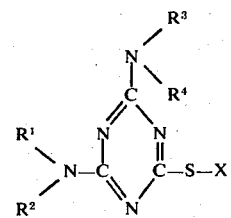

wherein $R^1$ and $R^3$ are each selected from the group consisting of hydrogen, alkyl, alkenyl, cycloalkyl, phenyl, aralkyl and substituted alkyl, alkenyl, cycloalkyl, phenyl and, aralkyl wherein the substituents are selected from the group consisting of —OH, —OR and —CN, R being alkyl with up to 18 carbon atoms, $R^2$ and $R^4$ are each selected from the group consisting of hydrogen, alkyl, alkenyl, cycloalkyl, phenyl, aralkyl and substituted alkyl, alkenyl, cycloalkyl, phenyl and aralkyl wherein the substituents are selected from the group consisting of —OH, —OR and —CN, R being alkyl with up to 18 carbon atoms, X is selected from the group consisting of (a) hydrogen,

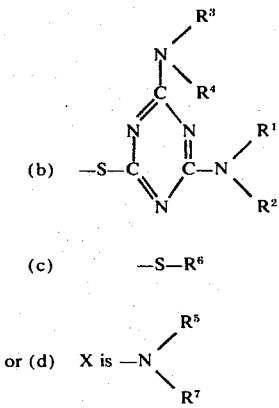

(c)  —S—$R^6$ , or (d) X is —N$\diagup^{R^5}_{\diagdown R^7}$ $R^6$ being selected from the group consisting of hydrogen, alkyl, aralkyl and cycloalkyl and $R^7$ being selected from the group consisting of alkyl, aralkyl and cycloalkyl and wherein $R^6$ and $R^7$ together may also form a cycloaliphatic ring having from 5 to 7 carbon atoms in the ring and from 5 to 10 carbon atoms, including lower alkyl, attached to the ring or wherein $R^6$ and $R^7$ may be linked by a member of the group consisting of —O—, —S— and

and wherein the number of carbon atoms in $R^1$, $R^2$, $R^3$, $R^4$, $R^6$ and $R^7$ is as follows:
 alkyl: up to 18 carbon atoms
 alkenyl: up to 6 carbon atoms
 cycloalkyl: from 5 to 7 carbon atoms
 aralkyl: from 7 to 9 carbon atoms.

Also in a given case one or more known vulcanization accelerators can be used in addition in the elastomer mixture.

As has furthermore been found the use of the reaction products of the invention can be advantageously combined with the addition of specific sulfur containing silanes which are described in Belgian Pat. No. 787,691 and Meyer-Simon U.S. Pat. No. 3,842,111.

The entire disclosure of Meyer-Simon is incorporated by reference and relied upon. This combined use of two very different reinforcing additives is of especial advantage for example in the production of tread strips for vehicle tires. Such silanes include for example bis-(3-triethoxysilylpropyl)-trisulfide, bis-(3-triethoxysilylpropyl)-tetrasulfide, bis-(3-trimethoxysilylpropyl)-trisulfide, bis-(3-trimethoxysilylpropyl)-tetrasulfide, bis-(3-diethoxy ethylsilylpropyl)-trisulfide, bis-(3-diethoxy ethylsilylpropyl)-tetrasulfide or any of the other silanes shown in Meyer-Simon, for example those set forth on column 2, line 56 to column 3, line 39. Thus the silanes can have the formula Z-alk-$S_n$-alk-Z in which Z is:

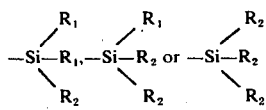

and in which $R_1$ is an alkyl group of 1 to 4 carbon atoms or phenyl and $R_2$ is an alkoxy group with 1 to 8, preferably 1 to 4, carbon atoms, a cycloalkoxy group with 5 to 8 carbon atoms or a straight or branched chain alkylmercapto group with 1 to 8 carbon atoms. All the $R_1$ and $R_2$ groups can be the same or different. Alk is a divalent hydrocarbon group with 1 to 18 carbon atoms. It can be straight or branched chain and can be a saturated aliphatic hydrocarbon group, an unsaturated aliphatic hydrocarbon group or a cyclic hydrocarbon group. Preferably alk has 1 to 6, most preferably 2 or 3 carbon atoms and $n$ is a number of 2 to 6, especially 2 to 4, most preferably 3 to 4. Mixtures of the silanes can be used.

In industrial rubber processing it is more and more preferred to order frm manufacturers already premixed constituents of the later rubber mixtures. The objects of the invention therefore also include the preparation of the following mixtures or premixtures and their use in the production of cross-linkable elastomer mixtures.

A mixture consisting of at least one of the reaction products of the invention and at least one light filler used in the rubber processing industry wherein the weight ratio of the both constituents of the mixture is in the range of for example 3:1 to 1:3 can be used for example.

Mixtures consist of at least one of the reaction products of the invention, at least one light filler used in the rubber processing industry and at least one elastomer of the group of natural and synthetic rubbers vulcanizable with sulfur.

Industrial areas of use for the described elastomer mixtures are for example, vehicle tires, especially automobile tires, including special cross-country tires, and airplane tires, namely both for the foundation (carcass), the belt and the tread surface (tread strip) of the tires; additionally industrial rubber articles as for example cable jackets, hoses, transmission belts, V-belts, conveyor belts, roll covers, sealing rings, cushioning elements and many more; additionally sole materials for shoes. The new elastomer mixtures have also been found suitable for glass fiber adhesive mixtures and the like.

Unless otherwise indicated all parts and percentages are by weight.

The quality improving effect of the reaction products of the invention are illustrated in the following examples.

EXAMPLE I

To a base mixture of the following composition

| Constituent | Amount in parts by weight |
|---|---|
| styrene-butadiene rubber (SBR 1500) | 100 |
| finely divided precipitated silica (Ultrasil VN 3 of Degussa) | 50 |
| zinc oxide (red seal quality) | 3 |
| stearic acid | 1 |
| N-cyclohexyl-2-benzothiazole-sulfenamide | 1 |
| diphenyl guanidine | 1.5 |
| sulfur | 2 | there were added the following reaction products of the invention by mixing with the filler. Each time there was used 10 parts by weight of the compound of the invention, a 1. Reaction product prepared by Example 1,
a 2. Reaction product prepared by Example 3,
a 3. Reaction product prepared by Example 2,
b 1. Reaction product of 3,6-methano-4,4-bis-(hydroxymethyl)-cyclohexene with sulfur in the mole ratio of 1:1.78 having 25 weight percent sulfur,
b 2. Reaction product of 3,6-methano-4,4-bis-(hydroxymethyl)-cyclohexene with sulfur in the mole ratio of 1:1 with 17.2 weight percent sulfur,
b 3. Reaction product of the same starting materials as in b(1) but in the mole ratio of 1:2 with a sulfur content of 29.4%,
b 4. Reaction product prepared by example 4,
c 1. Reaction product prepared by Example 5,
c 2. Starting materials as in c(1) but in the mole ratio of 1:2 with a sulfur content of 28.8 weight percent,
c 3. Starting materials as in c(1) but in the mole ratio of 1:4 with a sulfur content of 45.0 weight percent,
d 1. Reaction product of 2-methyl-4,4-bis-(hydroxymethyl) cyclohexene with sulfur in the mole ratio of 1:2 with a sulfur content of 26.0 weight percent.

The viscosity lowering effect of the reinforcing additive is plainly evident from the following Table 1. By the addition of 10 parts of the reinforcing additive the Mooney viscosity falls about 100 units and therewith into the viscosity range which is customary for furnace black filled vulcanizates.

Simultaneously, as is evident from following Table 2, the physical properties of the vulcanizate are changed favorably. Thus the tensile strength increase, the modulus level becomes increased depending on the structure of the gem dimethylol compound which is treated with sulfur and the sulfur content of the reaction product, likewise the Shore hardness is increased. The elongation at break behavior is inverse to the moduli and the rebound values (impact resilience) decreases, according to the increased filler activity. It is also clearly evident from Table 2 that the DIN (German Industrial Standard) abrasion is improved.

TABLE 1

| Mixture Containing Reaction Product According to | Mooney Viscosity, ML 4 |
|---|---|
| a (1) | 91 |
| a (2) | 92 |
| a (3) | 92 |
| b (1) | 91 |
| b (2) | 95 |
| b (3) | 90 |
| b (4) | 89 |
| c (1) | 84 |

TABLE 1-continued

| Mixture Containing Reaction Product According to | Mooney Viscosity, ML 4 |
|---|---|
| c (2) | 88 |
| c (3) | 92 |
| d (1) | 82 |
| No additive | 182 |

TABLE 2

| Reaction Product Containing Mixture | Heating Time in Minutes | Tensile Strength in kp/cm$^2$ | Modulus 300 in kp/cm$^2$ | Elongation At Break in % | Rebound in % | Shore-A-Hardness | In kp/cm Tear Propagation Resistance | Abrasion in mm$^3$ |
|---|---|---|---|---|---|---|---|---|
| No mixing | 60 | 197 | 39 | 665 | 34 | 76 | 18 | 170 |
| a (1) | 60 | 238 | 65 | 625 | 28 | 77 | 17 | 150 |
| a (2) | 55 | 198 | 111 | 443 | 26 | 79 | 11 | 131 |
| a (3) | 60 | 234 | 129 | 480 | 26 | 82 | 9 | 142 |
| b (1) | 45 | 224 | 52 | 643 | 27 | 86 | 20 | 150 |
| b (2) | 40 | 196 | 41 | 655 | 28 | 75 | 20 | 148 |
| b (3) | 50 | 208 | 66 | 573 | 29 | 76 | 14 | 135 |
| b (4) | 60 | 239 | 96 | 503 | 29 | 77 | 10 | 139 |
| c (1) | 45 | 237 | 47 | 673 | 28 | 70 | 19 | 135 |
| c (2) | 45 | 258 | 67 | 640 | 29 | 72 | 17 | 130 |
| c (3) | 60 | 256 | 99 | 535 | 28 | 76 | 13 | 122 |
| d (1) | 60 | 233 | 58 | 610 | 27 | 72 | 14 | 134 |

EXAMPLE II

In a base mixture of the following composition

| Constituent | Amount in Parts by Weight |
|---|---|
| natural rubber (ribbed smoked sheets No. 1 of a Defo hardness of 800) | 100 |
| finely divided, precipitated pure silica (Ultrasil VN 3 of Degussa) | 50 |
| zinc oxide (red seal quality) | 3 |
| stearic acid | 2 |
| N-cyclohexyl-2-benzothiazole-sulfenamide | 0.8 |
| diphenyl guanidine | 1.5 |
| sulfur | 2.5 | there were again added each time 10 parts by weight of the named reaction products of the invention, namely admixture with the filler (silica).

From Table 3 belonging to Example II it can be seen how the properties of natural rubber vulcanizates can be influenced with the help of the reinforcing additives of the invention. As in styrene-butadiene rubber (SBR 1500) also in natural rubber the tensile strength increases around 30 to 50 kp/cm$^2$, the modulus at 300% increases above all depending on the sulfur content of the reaction product, the elongation at break is influenced to a relatively minor extent, on the contrary the elasticity of the vulcanizate is significantly lowered according to the increased filler activity. The Shore hardness and tear propagation resistance are generally increased, and the DIN abrasion is strongly reduced.

TABLE 3

| Reaction Product Containing Mixture | Heating Time in Minutes | Tensile Strength in kp/cm$^2$ | Modulus 300 in kp/cm$^2$ | Elongation At Break in % | Rebound in % | Shore A-Hardness | In kp/cm Tear Propagation Resistance | Abrasion in mm$^3$ |
|---|---|---|---|---|---|---|---|---|
| No mixing | 80 | 213 | 41 | 670 | 44 | 70 | 47 | 241 |
| a (1) | 40 | 244 | 55 | 665 | 32 | 79 | 58 | 195 |
| a (2) | 45 | 243 | 72 | 630 | 34 | 81 | 42 | 142 |
| a (3) | 40 | 244 | 95 | 550 | 37 | 75 | 59 | 153 |
| b (1) | 40 | 260 | 57 | 680 | 32 | 77 | 54 | 196 |
| b (2) | 40 | 254 | 58 | 670 | 34 | 76 | 45 | 218 |
| b (3) | 45 | 259 | 68 | 630 | 34 | 76 | 52 | 206 |
| b (4) | 45 | 254 | 80 | 600 | 34 | 79 | 33 | 174 |
| c (1) | 26 | 267 | 54 | 675 | 29 | 67 | 57 | 184 |
| c (2) | 30 | 257 | 62 | 645 | 31 | 72 | 59 | 204 |
| c (3) | 30 | 248 | 72 | 615 | 32 | 78 | 58 | 180 |
| d (1) | 30 | 247 | 58 | 645 | 30 | 69 | 52 | 155 |

EXAMPLE III

Three mixtures are used in this example. Mixture 1 is a conventional rubber mixture for the production of treads (tread strips) for automobile tires. It contained the reinforcing black N339.

Mixture 2 contains the reinforcing additive of the invention made in Example 2. With the help of this reinforcing additive Mixture 2 was so made up that the vulcanizate from Mixture 2 reached the same modulus level as the vulcanizate from Mixture 1. Mixture 2 according to the invention contained no carbon black but as a light filler an active, precipitated silica.

The Mixture 3 contained as a comparison mixture to Mixture 2 no additive of the invention (omission of the reinforcing additive). The three mixtures had the following compositions:

| Constituent (in parts by weight) | Mixture 1 | Mixture 2 | Mixture 3 |
|---|---|---|---|
| styrene-butadiene rubber (SBR 1712) | 137.5 | 137.5 | 137.5 |
| carbon black N339 | 80 | — | — |
| finely divided, precipitated | | | |

-continued

| Constituent (in parts by weight) | Mixture 1 | Mixture 2 | Mixture 3 |
|---|---|---|---|
| silica (Ultrasil VN 3 of Degussa) | — | 80 | 80 |
| reaction product of Example 2 | — | 6 | — |
| zinc oxide | 4 | 4 | 4 |
| stearic acid | 1.2 | 1.2 | 1.2 |
| phenyl-B-naphthylamine | 1.5 | 1.5 | 1.5 |
| N-isopropyl-N'-phenyl-p-phenylenediamine | 1.5 | 1.5 | 1.5 |
| N-tert. butyl-2-benzothiazyl sulfenamide | 1.2 | — | — |
| 2-ethylamino-4-diethylamino-6-mercapto-s-triazine | — | 2.0 | 2.0 |
| sulfur | 1.4 | 0.5 | 0.5 |

First the corresponding premixtures 1 to 3 which did not contain sulfur or an accelerator were produced at a flow temperature of 80°C. in an internal mixer (Type GK2 of Werner and Pfleiderer, Stuttgart-Feuerbach) according to the "Upsidedown Process".

The final mixtures were also produced after a 24-hour intermediate storage in a kneader (internal mixer) at a flow temperature of 80°C.

The vulcanization took place at 160°C. for a period of 40 minutes.

The measured properties of the vulcanizate are given in the following Table 4.

TABLE 4

|  | Mixture 1 | Mixture 2 | Mixture 3 |
|---|---|---|---|
| Tensile strength (measured according to DIN 53504) | 204 | 198 | 11 |
| Modulus 300 (according to DIN 53504) | 104 | 98 | 7 |
| Elongation at break (according to DIN 53504) | 470 | 490 | 1100 |
| Tear Propagation resistance (according to DIN 53507) | 9 | 17 | 16 |
| Rebound (according to DIN 53512) | 23 | 29 | 31 |
| Shore A-Hardness (according to DIN 53504) | 64 | 73 | 68 |

From Table 4 it is clear that at the same modulus level of mixtures 1 and 2, the Mixture 2 has the higher tear strength, the higher Shore A hardness and the higher elasticity.

It is worthy of note that the comparison Mixture 3 whose Mooney viscosity is clearly higher than that of Mixtures 1 and 2 results in a vulcanizate which in no way satisfies the requirements for tensile strength and modulus.

EXAMPLES IV AND V

These examples show the utility of the new reinforcing additive in polymer blends wherein in Example IV there is used a blend of natural rubber with polybutadiene and in Example V there is used a blend of styrene-butadiene rubber with polybutadiene.

In both mixtures 1 and 2 there were used tire tread compositions for winter tires with strong grip on snow and ice.

| Constituents (in parts by weight) | Mixture 1 | Mixture 2 |
|---|---|---|
| natural rubber (RSS I, Defo hardness 800) | 30 | — |
| styrene-butadiene rubber (SBR 1507) | — | 30 |
| polybutadiene with high cis-1,4 content (Buna CB 10) | 70 | 70 |
| silica (Ultrasil VN 3 of Degussa) | 100 | 100 |
| Reaction product of Example 1 | 10 | 14 |
| Reaction product of Example 2 | 10 | 6 |
| zinc oxide | 4 | 4 |
| stearic acid | 1 | 1 |
| phenyl-α-naphthylamine | 1.5 | 1.5 |
| N-isopropyl-N'-phenyl-p-phenylenediamine | 1.5 | 1.5 |
| plasticizer (naphthenic hydrocarbons) | 70 | 70 |
| sulfur | 1 | 0.8 |
| 4-dimethylamino-2,6-bis-(dimethylaminothio)-s-triazine | 3 | 3 |
| 2-ethylamino-4-diethylamino-6-mercapto-s-triazine | 1.5 | 1.5 |
| tetramethyl thiurammonosulfide | 0.2 | 0.2 |

Mixing procedure: Upsidedown process (as in Example III).

The vulcanization was carried out at 160°C. The vulcanization time was fixed according to the Vulcameter optimum.

|  | Mixture 1 | Mixture 2 |
|---|---|---|
| Prevulcanization time $t_s$ measured in minutes (according to DIN 53524) at 130°C. (Mooney Scorch) | 14.1 | 12.9 |
| Prevulcanization time $t_{35}$ in minutes (130° C. Mooney Cure) | 17.9 | 17.3 |
| Mooney plasticity at 100°C., Standard rotor, time of test: 4 minutes (ML4) | 88 | 87 |
| Tensile strength (see Example I) | 91 | 97 |
| 300% Modulus (see Example I) | 62 | 63 |
| Elongation at break in % | 463 | 477 |
| Tear Propagation Resistance (See Example I) | 23 | 27 |
| Rebound (See Example I) | 27 | 26 |
| Shore A hardness | 78 | 77 |

| | Mixture | |
|---|---|---|
| | 1 | 2 |
| Abrasion in mm³ (DIN Abrasion) | 108 | 108 |

Treads (tread strips) for winter tires were produced from both mixtures and the tires tested on a smooth winter-like ice surface in comparison with tires which had a carbon black filled standard automobile tread surface wherein for the standard tires there was fixed a friction value of 100 (%). With the automobiles which were always equippd with four of the same tires there were determined the acceleration value, the circular acceleration value and the deceleration value and from these the friction value (as an average) calculated. The friction values ($\mu$ value) on smooth ice at $-5°C$. for the tires of examples IV and V were 118 and 120% respectively.

EXAMPLES VI AND VII

Examples VI and VII relate to the following mixtures 1 and 2 for the production of ice slip resistant winter tread surfaces of automobile tires. In these mixtures there are blends of two different reaction products of the invention which also contain a reinforcing additive based on a silane.

In regard to the properties of the vulcanizates, the mixtures correspond to those of Examples IV and V and, hence, are typical of skid resistant winter tire tread mixtures, and differ therefrom on account of the addition of the second reinforcing additive based on a silane in that they result in lower Shore hardnesses and higher elasticities.

| | Mixture | |
|---|---|---|
| Constituent (in parts by weight) | 1 | 2 |
| natural rubber (RSS I, Defo hardness 800) | 30 | — |
| styrene-butadiene rubber (SBR 1507) | — | 30 |
| polybutadiene with high cis-1,4-content (Buna CB 10) | 70 | 70 |
| silica (Ultrasil VN3 of Degussa) | 100 | 100 |
| mixture of equal parts of a precipitated silica (Ultrasil VN 3 of Degussa) and bis-(3-triethoxysilylpropyl)-tetrasulfide | 10 | 10 |
| reaction product of Example 1 | 5 | 5 |
| reaction product of Example 2 | 5 | 4 |
| zinc oxide | 4 | 4 |
| stearic acid | 1 | 1 |
| phenyl-α-naphthylamine | 1.5 | 1.5 |
| N-isopropyl-N'-phenyl-p-phenylenediamine | 1.5 | 1.5 |
| plasticizer (napthenic hydrocarbons) | 70 | 70 |
| sulfur | 0.5 | 0.3 |
| 2,4-bis-(N-dimethylsulfenamido)-6-dimethylamino-s-triazine | 1.2 | 1.2 |
| 2-ethylamino-4-diethylamino-6-mercapto-s-triazine | 1.3 | 1.4 |

The vulcanization was carried out at 160°C. The vulcanization times which varied between 20 and 60 minutes were chosen as optimum from the vulcameter curve.

The properties of both mixtures and their vulcanizates are shown in the following Table:

| | Mixtures | |
|---|---|---|
| | 1 | 2 |
| Prevulcanization time $t_5$ measured in minutes (according to DIN 53524) at 130°C. (Mooney Scorch) | 17.8 | 17.5 |
| Prevulcanization time $t_{35}$ in minutes (130°C. Mooney cure) | 27.7 | 27.0 |
| Mooney plasticity at 100°C., standard rotor, time of test: 4 minutes (ML 4) | 85 | 87 |
| Tensile strength (see Example 1) | 101 | 97 |
| 300% Modulus (see Example 1) | 61 | 58 |
| Elongation at break in % | 510 | 525 |
| Tear Propagation Resistance (See Example 1) | 25 | 22 |
| Rebound (see Example 1) | 29 | 29 |
| Shore A-hardness | 71 | 69 |
| Abrasion in mm³ (DIN abrasion) | 76 | 82 |

The figures above show that mixtures of the reaction products of the invention with selected silanes may also be successfully used in the vulcanizable rubber mixtures.

Figure 3:
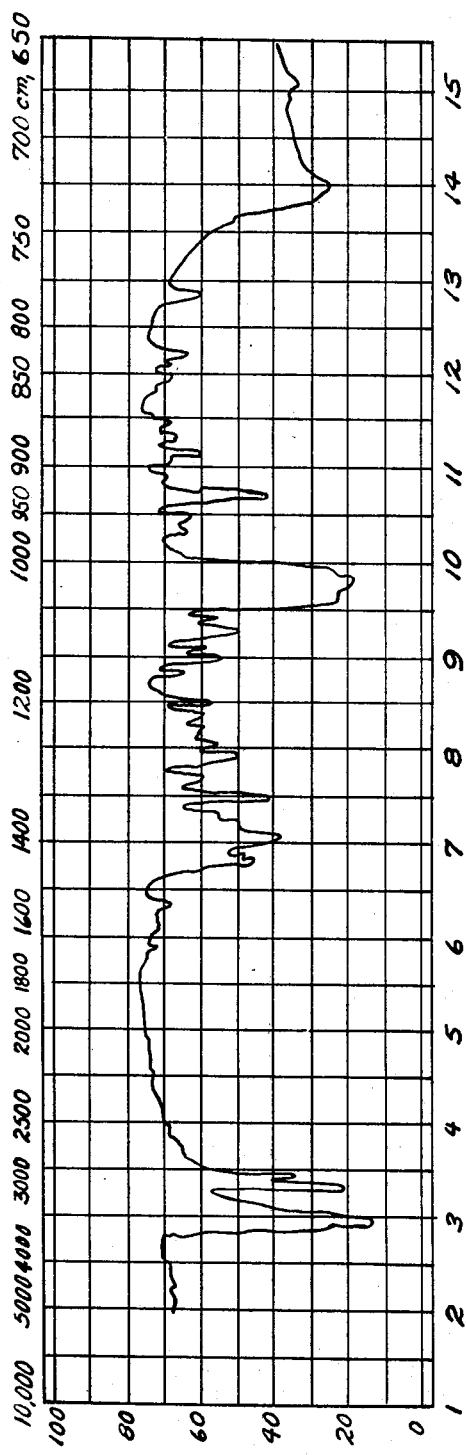

In the attached drawings FIGS. 1 through 4 there are given the IR spectra of two reaction products according to the invention or reinforcing additives (FIGS. 2 and 4) and their starting compounds (FIGS. 1 and 3).

FIG. 1 contains the infrared spectrum of 4,4-bis-(hydroxymethyl)-cyclohexene itself (M.P. 94° to 96°C.). The sulfurizaton product produced therefrom containing 31 weight percent sulfur (see Example 1) has the IR spectrum of FIG. 2.

FIG. 3 is the IR spectrum of 3,3-methano-4,4-bis-(hydroxymethyl)-cyclohexene with the formula

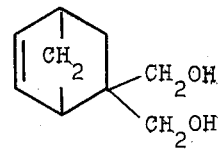

Figure 4:
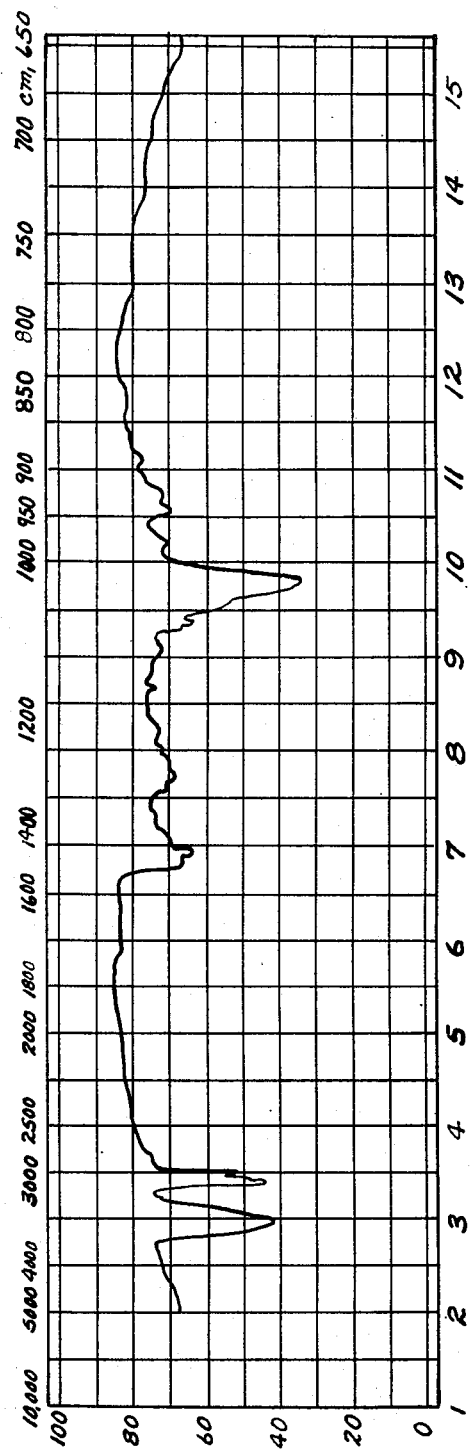

The IR spectrum in FIG. 4 is that of the sulfurization product produced from this diol and sulfur in a molar reaction ratio of 1:8 (see Example 4).

All IR spectra were taken with the infrared spectrophotometer 21 of the firm Perkin-Elmer using a NaCl prism (slit program 927; time constant 1; intensification 5; speed 4 minutes per micron; damping 1; scale 1 micron = 5 cm).

From the curves it is clear that through the sulfurization process the characteristic double bond band at $3.3\lambda = 3030$ cm$^{-1}$ has practically completely disappeared.

What is claimed is:

1. A composition comprising (1) the sulfur containing reaction products of (a) a 4,4-bis-(hydroxymethyl)-cyclohexene compound of the formula

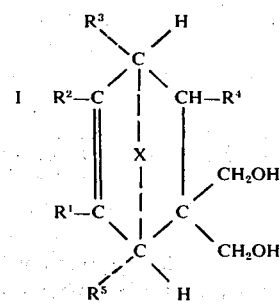

where $R^1$, $R^2$ and $R^4$ are hydrogen, methyl or phenyl and there is also present either (1) X as the bridging member methylene or ethylene or (2) X is absent and there are present both $R^3$ and $R^5$ wherein $R_3$ and $R^5$ are hydrogen, methyl or phenyl with (b) sulfur as a reinforcing additive for (2) a light reinforcing filler, said composition containing (1) and (2) being suitable for use in a cross-linkable elastomer which is capable of cross-linking by sulfur or a peroxide.

2. The composition of claim 1 wherein the light filler is silica, silicate, aluminum oxide, titanium oxide, calcium carbonate, zinc sulfide, barium sulfate or mixtures thereof.

3. The composition of claim 2 wherein the filler is silica or a silicate.

4. The composition of claim 3 wherein the filler is silica.

5. The composition of claim 1 wherein (1) and (2) are used in the weight ratio of 3:1 to 1:3.

6. A composition comprising (1) the sulfur containing reaction product of (a) a 4,4-bis-(hydroxymethyl)-cyclohexene compound of the formula

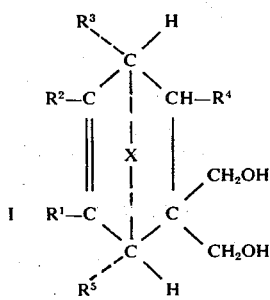

where $R^1$, R2 and $R^4$ are hydrogen, methyl or phenyl and there is also present either (1) X as the bridging member methylene or ethylene or (2) X is absent and there are present both $R^3$ and $R^5$ wherein $R^3$ and $R^5$ are hydrogen, methyl or phenyl with (b) sulfur as a reinforcing additive for (2) a light reinforcing filler, said composition containing in addition to (1) and (2) an elastomer cross-linkable with sulfur or a peroxide.

7. The product prepared by vulcanizing the composition of claim 6.

8. The composition of claim 6 wherein the elastomer comprises a diene rubber.

9. The composition of claim 8 wherein the elastomer comprises natural rubber, polybutadiene, polyisoprene, butadiene-styrene copolymer, butadiene-acrylonitrile copolymer, polychlorobutadiene, butyl rubber, halogenated butyl rubber, ethylene-propylene-non-conjugated diene terpolymer, transpolypenteneamer or carboxyl rubber.

10. The composition of claim 9 wherein the elastomer comprises natural rubber, polybutadiene or butadiene-styrene copolymer.

11. The composition of claim 6 which does not contain carbon black.

12. The composition of claim 6 wherein the filler elastomer mixture also contains carbon black in an amount of 0.05 to 50 parts by weight per 100 parts by weight of elastomer.

13. The composition of claim 6 wherein the elastomer comprises a sulfur vulcanizable natural or synthetic rubber.

14. The composition of claim 12 wherein there is employed 1 to 1000 parts by weight of the light-reinforcing filler per 100 parts of elastomer.

15. The composition of claim 6 wherein there is employed 1 to 1000 parts by weight of the light reinforcing filler per 100 parts of elastomer.

16. The composition of claim 15 wherein the light reinforcing filler is a finely divided, active, precipitated silica.

17. The composition of claim 16 wherein there is used 40 to 500 parts by weight of the silica per 100 parts by weight of elastomer.

18. The composition of claim 6 including a vulcanization accelerator of the formula

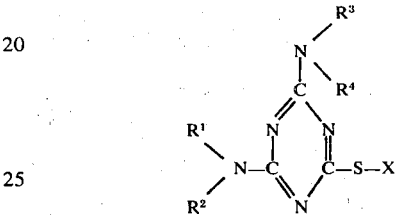

wherein $R^1$ and $R^3$ are each selected from the group consisting of hydrogen, alkyl, alkenyl, cycloalkyl, phenyl, aralkyl and substituted alkyl, alkenyl, cycloalkyl, phenyl and, aralkyl wherein the substituents are selected from the group consisting of —OH, —OR and —CN, R being alkyl with up to 18 carbon atoms, $R^2$ and $R^4$ are each selected from the group consisting of hydrogen, alkyl, alkenyl, cycloalkyl, phenyl, aralkyl and substituted alkyl, alkenyl, cycloalkyl, phenyl and aralkyl wherein the substituents are selected from the group consisting of —OH, —OR and —CN, R being alkyl with up to 18 carbon atoms, X is selected from the group consisting of (a) hydrogen,

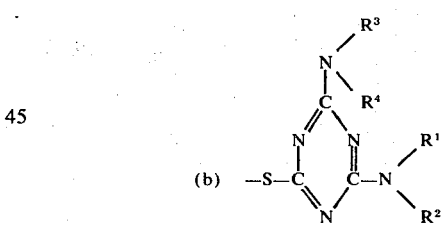

(c)      —S—$R^6$ ,

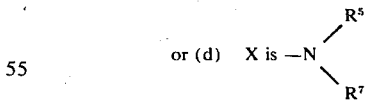

$R^6$ being selected from the group consisting of hydrogen, alkyl, aralkyl and cycloalkyl and $R^7$ being selected from the group consisting of alkyl, aralkyl and cycloalkyl and wherein $R^6$ and $R^7$ together may also form a cycloaliphatic ring having from 5 to 7 carbon atoms in the ring and from 5 to 10 carbon atoms, including lower alkyl, attached to the ring or wherein $R^6$ and $R^7$ may be linked by a member of the group consisting of —O—, —S— and

and wherein the number of carbon atoms in $R^1$, $R^2$, $R^3$, $R^4$, $R^6$ and $R^7$ is as follows:
  alkyl: up to 18 carbon atoms
  alkenyl: up to 6 carbon atoms
  cycloalkyl: from 5 to 7 carbon atoms
  aralkyl: from 7 to 9 carbon atoms.

19. The composition of claim 18 wherein X is (a), (b) or (d).

20. The composition of claim 18 wherein X is hydrogen.

21. The composition according to claim 20 wherein $R^1$, $R^2$, $R^3$, and $R^4$ are hydrogen or lower alkyl.

22. The composition of claim 21 wherein $R^1$ is hydrogen, $R^2$ is lower alkyl, $R^3$ is hydrogen or lower alkyl and $R^4$ is lower alkyl.

23. The composition of claim 18 wherein X is (b).

24. The composition of claim 23 wherein $R^1$, $R^2$, $R^3$ and $R^4$ are hydrogen or lower alkyl.

25. The composition of claim 24 wherein $R^1$ is hydrogen, $R^2$ is lower alkyl, $R^3$ is hydrogen or lower alkyl and $R^4$ is lower alkyl.

26. The composition of claim 6 including a sulfur containing adhesion promoting agent of the formula
  Z-alk-$S_n$-alk-Z in which Z is:

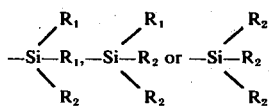

and in which $R_1$ is an alkyl group of 1 to 4 carbon atoms or phenyl and $R_2$ is an alkoxy group with 1 to 8 carbon atoms of a cycloalkoxy group with 5 to 8 carbon atoms, alk is a divalent hydrocarbon group with 1 to 18 carbon atoms and $n$ is a number of 2 to 6.

27. The composition of claim 26 wherein $R_1$ and $R_2$ have 1 to 4 carbon atoms and $n$ is 2 to 4.

28. The composition of claim 26 wherein Z is

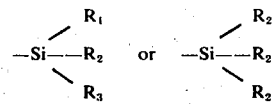

29. The composition of claim 28 wherein $R_1$ and $R_2$ have 1 to 8 carbon atoms.

30. The composition of claim 29 wherein Z is

and $R_2$ has 1 to 4 carbon atoms.

31. The composition of claim 18 also including a sulfur containing adhesion promoting agent of the formula
  Z-alk-$S_n$-alk-Z in which Z is:

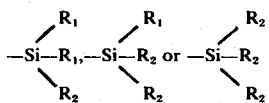

and in which $R_1$ is an alkyl group of 1 to 4 carbon atoms or phenyl and $R_2$ is an alkoxy group with 1 to 8 carbon atoms of a cycloalkoxy group with 5 to 8 carbon atoms, alk is a divalent hydrocarbon group with 1 to 18 carbon atoms and $n$ is a number of 2 to 6.

32. The composition of claim 6 containing (1) in an amount of 0.05 to 100 parts by weight per 100 parts by weight of elastomer.

33. The composition of claim 32 wherein (1) is 0.5 to 25 parts per 100 parts by weight of elastomer.

34. The composition of claim 32 containing 1 to 1000 parts by weight of (2) per 100 parts of elastomer.

35. The composition of claim 32 wherein (1) and (2) are used in the weight ratio of 3:1 to 1:3.

* * * * *